United States Patent
Presente et al.

(10) Patent No.: US 6,465,201 B1
(45) Date of Patent: Oct. 15, 2002

(54) METHOD FOR RAPIDLY DETECTING AND ENUMERATING MICROORGANISMS IN MAMMALIAN CELL PREPARATIONS USING ATP BIOLUMINESCENCE

(75) Inventors: Esther Presente, Newton, MA (US); Barbara Young, Needham, MA (US); Susan Upperman, Westford, MA (US)

(73) Assignee: Millipore Corporation, Bedford, MA (US)

(*) Notice: Subject to any disclaimer, the term of this patent is extended or adjusted under 35 U.S.C. 154(b) by 0 days.

(21) Appl. No.: 09/574,124

(22) Filed: May 19, 2000

Related U.S. Application Data

(60) Provisional application No. 60/135,910, filed on May 25, 1999, now abandoned.

(51) Int. Cl.$^7$ .................................................. C12Q 1/66
(52) U.S. Cl. .............................. 435/8; 435/34; 435/259
(58) Field of Search ................................ 435/8, 18, 34, 435/39, 173.7, 173.8, 259

(56) References Cited

U.S. PATENT DOCUMENTS

| | | | |
|---|---|---|---|
| 5,366,867 A | * 11/1994 | Kawakami et al. | 435/8 |
| 5,766,868 A | 6/1998 | Seto | 435/8 |
| 5,891,702 A | * 4/1999 | Sakakibara et al. | 435/227 |
| 5,908,751 A | 6/1999 | Higo et al. | 435/6 |

FOREIGN PATENT DOCUMENTS

| | | |
|---|---|---|
| CH | 678 065 | 7/1991 |
| EP | 0 025 351 | 9/1980 |
| WO | WO 0 025 351 | * 3/1981 |

OTHER PUBLICATIONS

Health care solutions through microbiology; BACTEC 9000 Blood Culture System (9–Pages). No Date Avail.
Faster Results for Food Testing; BacT/Alert Microbial Detection System (5–Pages). No Date Avail.

* cited by examiner

*Primary Examiner*—Ralph Gitomer
(74) *Attorney, Agent, or Firm*—Nields & Lemack

(57) ABSTRACT

A method for rapidly detecting and enumerating microorganisms, having a level of microbial ATP, in the presence of mammalian cell preparations, comprising the steps of: providing a mammalian cell preparation comprising mammalian cells having a level of mammalian ATP; reducing the level of mammalian ATP in said cell preparation by, selectively lysing the mammalian cells and not lysing microbial cells with detergent or osmotic shock to extract the mammalian ATP, treating the extracted mammalian ATP with one or more ATP hydrolyzing compounds; and immobilizing the microorganisms and washing away said detergent and the hydrolyzing compound by filtering the mammalian cell preparation through a micropartioned hydrophilic/hydrophobic membrane; extracting the microbial ATP using an extracting reagent; drying the membrane; applying a bioluminescent reagent onto the membrane; and detecting and enumerating the microorganisms.

26 Claims, No Drawings

METHOD FOR RAPIDLY DETECTING AND ENUMERATING MICROORGANISMS IN MAMMALIAN CELL PREPARATIONS USING ATP BIOLUMINESCENCE

This application claims benefit of Provisional Application Serial No. 60/135,910 filed May 25, 1999 and now abandoned.

FIELD OF THE INVENTION

This invention relates to a method for rapidly reducing background adenosine triphosphate (ATP) in a mammalian cell preparation and detecting the presence or absence of microorganisms in the cell preparation using ATP bioluminescence.

BACKGROUND OF THE INVENTION

Protein-based biopharmaceutical products are often produced by cloning the desired genes into mammalian tissue culture cells and producing the protein products on a large scale in a mammalian cell fermentation facility. However, microbial contamination of mammalian cell fermentors results in cell death and leads to losses and delays in production. Proactive measures, such as monitoring cell culture production and detecting the presence of low levels of microorganism contamination, are useful to reduce loss of time and revenue.

Contaminating microorganisms are typically detected in cell culture by membrane filtration, followed by culturing on media until colonies are visible, or by sterility testing in liquid media. The culturing method typically does not produce results for several days and the standard sterility testing requires one to two weeks for results. Although other detection methods are known, including Polymerase Chain Reaction for detecting specific organisms such as Mycoplasma and methods for detecting general microbial contamination in the blood testing market such as BacT/Alert® from Organon Tecknika and Bactec™ from Becton Dickinson, these methods do not utilize ATP bioluminescence and do not have the sensitivity or speed of an ATP detection system.

SUMMARY OF THE INVENTION

It is therefore a primary object of this invention to provide a method for rapidly detecting and accurately enumerating microorganisms in mammalian cell preparations using ATP bioluminescence.

It is a further object of this invention to provide a highly sensitive method for rapidly and capably detecting and enumerating low levels of microorganisms in mammalian cell preparations.

It is a further object of this invention to provide a method of reducing ATP background in tissue culture cells for rapidly detecting and enumerating microorganisms in mammalian cell preparations using ATP bioluminescence.

It is a further object of the invention to provide a convenient method for preparing samples for detecting and enumerating microorganisms in mammalian cell preparations.

It is a further object of the invention to provide a method for detecting and enumerating microorganisms that quantifies the microbial organisms and automatically records and documents results.

It is a further object of the invention to provide a method for rapidly and capably detecting and enumerating low levels of microorganisms so that informed decisions can be made before expanding cultures or using cell lines for patient treatments.

It is a further object of the invention to provide a method for detecting and enumerating microorganisms in mammalian cell preparations in less than 24 hours.

A preferred method of the invention for rapidly detecting and enumerating microorganisms, having a level of microbial ATP, in mammalian cell preparations, comprises the steps of: providing a mammalian cell preparation comprising mammalian cells having a level of mammalian ATP; reducing the level of mammalian ATP in the cell preparation by, differentially lyzing the mammalian cells with one or more detergents to extract the mammalian ATP, treating the extracted mammalian ATP with one or more ATP hydrolyzing enzymes, such as adenosine triphosphatase (ATPase); immobilizing the microorganisms and washing away the detergent and the ATPase by filtering the mammalian cell preparation through a micropartitioned hydrophilic/hydrophobic membrane; extracting the microbial ATP using an extracting reagent; applying a bioluminescent reagent onto the membrane; and detecting and enumerating the microorganisms. The method may further comprise, after the extracting step, the step of drying the membrane at temperatures between about ambient temperature to 40° C.

The method, after the step of lyzing the mammalian cells, may further comprise the step of incubating the cell preparation for about 15 minutes at room temperature; and after the step of filtering the cell preparation, may further comprise the step of incubating the cell preparation for about 8–24 hours at 25–35° C.

The detergents preferably comprise one or more detergents selected from a group consisting of 2% Tween 80, 13% Tween 80, Milli-Q water and 0.005% Triton X-100 with or without 10–5% SDS, and the bioluminescent reagent preferably comprises a luciferin-luciferase reagent. The microbial ATP extracting reagent preferably comprises either methanol, or ethanol, mixed with 0.1 to 5% by weight of ammonium hydroxide.

Another preferred method of the invention for rapidly detecting and enumerating microorganisms, having a level of microbial adenosine triphosphate (ATP), in mammalian cell preparations, comprises the steps of: providing a mammalian cell preparation comprising mammalian cells having a level of mammalian ATP; reducing the level of mammalian ATP in the cell preparation by, differentially lyzing the mammalian cells by osmotically shocking the cells in water to extract the mammalian ATP, treating the extracted mammalian ATP with one or more ATP hydrolyzing enzymes; immobilizing the microorganisms and washing away the hydrolyzing enzyme by filtering the mammalian cell preparation through a micropartitioned hydrophilic/hydrophobic membrane; extracting the microbial ATP using an extracting reagent; drying the membrane; applying a bioluminescent reagent onto the membrane; detecting and enumerating the microorganisms.

Similar to the first described preferred method, after the step of lyzing the mammalian cells, the method may further comprise the step of incubating the cell preparation for about 15 minutes at room temperature, and after the step of filtering the cell preparation, the method may further comprising the step of incubating the cell preparation for about 8–24 hours at 25–35° C.

The bioluminescent reagent preferably comprises a luciferin/luciferase reagent and the microbial ATP extracting reagent preferably comprises methanol, or ethanol, mixed with 0.1 to 5% by weight of ammonium hydroxide.

Yet another preferred method of the invention for rapidly detecting and enumerating microorganisms, having a level of microbial adenosine triphosphate (ATP), in mammalian cell preparations, comprising the steps of: providing a mammalian cell preparation comprising mammalian cells having a level of mammalian ATP; reducing the level of mammalian ATP in the cell preparation by, differentially lyzing the mammalian cells with one or more detergents to extract the mammalian ATP, incubating the cell preparation for about 15 minutes at room temperature, treating the extracted mammalian ATP with one or more ATP hydrolyzing enzymes during and/or after the incubation step; immobilizing the microorganisms and washing away the detergent and the hydrolyzing enzyme by filtering the mammalian cell preparation through a micropartitioned hydrophilic/hydrophobic membrane; incubating the cell preparation for about 8–24 hours at 25–35° C.; extracting the microbial ATP using an extracting reagent; drying the membrane; applying a luciferin/luciferase reagent onto the membrane; and detecting and enumerating the microorganisms.

Similar to the first described preferred method, the detergents preferably comprise one or more detergents selected from a group consisting of 2% Tween 80, 13% Tween 80, Milli-Q water and 0.005% Triton X-100 plus $10^{-5}$% SDS; and the microbial ATP extracting reagent preferably comprises methanol, or ethanol, mixed with 0.1 to 5% by weight of ammonium hydroxide.

Other objects, features and advantages will occur to those skilled in the art from the following description of the preferred methods.

DETAILED DESCRIPTION OF THE PREFERRED METHODS

The method of the invention is based on ATP bioluminescence and utilizes the light producing enzyme, luciferase, derived from fireflies for the rapid detection of microorganisms. The method may be used with any type of patient tissue cells including, but not limited to, stem cells. The method is expected to be useful for other biomedical products such as cell vaccines.

Contained within all living organisms is adenosine triphosphate (ATP), a storehouse of energy to fuel metabolic reactions. Like fireflies, the method of the invention utilizes luciferase to hydrolyze ATP to adenosine monophosphate (AMP), thereby releasing energy in the form of light. The amount of light emitted from each microbial colony forming unit is detected using Millipore Corporation's MicroStar™ Rapid Detection System.

To detect the presence or absence of microbial ATP in a cell preparation, the background mammalian ATP must be reduced. The method of the invention generally accomplishes reduction of background ATP using differential lysis by, first pretreating the mammalian cells with osmotic shock and/or a detergent or a cocktail of detergents, followed by controlled treatment with an ATP hydrolyzing enzyme, adenosine triphosphatase (ATPase). The cell preparation is then filtered through a partitioned microporous membrane to immobilize the microbial cells and to wash away the detergent and ATP hydrolyzing enzyme. After filtration, the membrane is incubated on media for 8–24 hours. After which, ATP bioluminescence reagents are applied and any resulting microbial light signals detected.

As noted, After obtaining the tissue cells, the tissue cells are pretreated by differential lysis with osmotic shock and/or a detergent or cocktail of detergents. Various differential lysis conditions are effective at substantially reducing the mammalian ATP levels while preserving the viability of the microbial cells. These differential lysis conditions include, but are not necessarily limited to, one or more rinses comprising one or more of the following: 13% Tween 80 (Polysorbate 80), 2% Tween 80, Milli-Q water and/or 0.005% Triton-X 100 with or without $10^{-5}$% SDS. In all conditions, there are preferably about $10^6$ tissue culture cells in 10 ml. The tissue culture cells are then incubated for 15 minutes at room temperature. Ten units of ATPase may be added either before or after the 15 minute incubation, but prior to filtration.

Filtration is accomplished by pouring the cell preparation preferably through a MicroStar™ Milliflex filtering unit containing the membrane, disclosed in U.S. Pat. No. 5,366,867, comprising a membrane filter comprising a film or sheet of a hydrophilic/hydrophobic filtration membrane attached to a plastic frame. The membrane is made up of a number of hydrophilic filter sections substantially completely isolated from each other with a lattice or circular hydrophobic micropartitions.

In the case of yeasts, the filter with the immobilized cells captured thereon may be treated immediately with bioluminescence reagent and tested for the presence of microbes. In the case of bacteria, the filter with the immobilized microbial cells captured thereon is preferably incubated on a liquid TSB cassette at 25–35° C. for 8–24 hours, preferably about 16 hours.

After incubation, the filters are dried and then are sprayed with an ATP extracting reagent preferably having a boiling point below 120° C. Useful extracting reagents include alcohols, ethers, esters and halogenized derivatives of methane, ethane, methylene or ethylene, as well as acetonitrile and triethylamine. Methanol and ethanol are preferred. The microbial ATP extracting reagent may be further enhanced by mixing 0.1 to 5% by weight of hydrochloric acid, organic acids having a boiling point below 120° C., or basic compounds such as ammonium hydroxide and organic amines, although ammonium hydroxide is preferred. Depending on the species of microbes to be tested, after a period between 5 seconds and 5 minutes, the ATP extracting reagent is subsequently evaporated off at temperatures between ambient temperature and 40° C.

After evaporation, a luminescence-inducing reagent of luciferin/luciferase is sprayed or applied with a pipette onto the membrane filter. The treated filter is then exposed to Millipore Corporation's MicroStar™ Rapid Detection System by which any microbial light signals are detected and enumerated and the results recorded and documented by the system. The total time period for preparation of the sample and detection to the end result is less than 24 hours.

Other than Milli-Q water, all of the detergents, ATP extracting reagents and bioluminescence reagents described herein are available through Sigma-Aldrich. Milli-Q is a product of Millipore Corporation.

Following are four additional examples of preferred methods of the invention.

EXAMPLE A

1. Add 9 ml of sterile MilliQ water to a sterile 15 ml conical tube.
2. Add 1 ml of cells (about $10^6$).
3. Add 10 U of Apyrase (100 U dissolved in 1 ml of sterile Butterfields buffer).
4. Vortex.
5. Incubate at room temperature for 15 minutes.
6. Set up a Milliflex manifold with Milliflex MicroStar units containing about 50 ml of sterile MilliQ water.

7. Add sample and filter.
8. Rinse with 10 ml sterile 2% Tween 80.
9. Rinse twice with 50 ml of sterile MilliQ water.
10. Place on a liquid media cassette containing TSB.
11. Incubate at 30° C. for 17 hours.
12. Following incubation, dry membranes in a biological hood.
13. Apply ATP releasing agent.
14. Dry.
15. Apply bioluminescence reagent.
16. Detect for 15 seconds.

To spike the samples, follow steps 1–3, then add 100 µl of $10^{-5}$ dilution of an overnight culture of B. subtilis, ATCC# 6633. Continue with steps 4–16.

EXAMPLE B

1. Add 9 ml of 13% sterile Tween 80 to a sterile 15 ml conical tube.
2. Follow steps 2–16 of Example A.

EXAMPLE C

1. Add 9 ml of sterile MilliQ water to a sterile 15 ml conical tube.
2. Add 50 µl of 1% sterile Triton X-100 to achieve a final concentration of 0.005%.
3. Follow steps 2–16 of Example A.

EXAMPLE D

1. Add 9 ml of sterile MilliQ water to a sterile 15 ml conical tube.
2. Add 50 µl of 1% sterile Triton X-100 to achieve a final concentration of 0.005%.
3. Add 10 µl of 0.01% sterile SDS to achieve a final concentration of $10^{-5}$%.
4. Follow steps 2–26 of Example A.

Slight modifications of the methods will occur to those skilled in the art and are within the following claims:

What is claimed is:

1. A method for rapidly detecting and enumerating microorganisms, having a level of microbial adenosine triphosphate (ATP), in mammalian cell cultures, comprising the steps of,
    providing a mammalian cell culture comprising mammalian cells having a level of mammalian ATP;
    reducing said level of mammalian ATP in said cell culture by,
        selectively lysing said mammalian cells and not lysing microbial cells with one or more detergents to extract said mammalian ATP, and
        treating said extracted mammalian ATP with one or more ATP hydrolyzing enzymes;
    immobilizing said microorganisms and washing away said detergent and said hydrolyzing enzyme by filtering said mammalian cell preparation through a micropartioned hydrophilic/hydrophobic membrane;
    extracting said microbial ATP using an extracting reagent;
    applying a bioluminescent reagent onto said membrane; and
    detecting and enumerating said microorganisms.

2. The method of claim 1, after said step of lyzing said mammalian cells, further comprising the step of incubating said cell preparation for about 15 minutes at room temperature.

3. The method of claim 1, after said step of filtering said cell culture, further comprising the step of incubating said membrane, through which said cell culture was filtered, for about 8–24 hours at about 25–35° C.

4. The method of claim 1, after said extracting step, further comprising the step of drying said membrane at temperatures between about ambient temperature to 40° C.

5. The method of claim 1, wherein said detergents comprise one or more detergents selected from the group consisting of 2% Polyoxyethylenesorbitan Monooleate, 13% Polyoxyethylenesorbitan Monooleate, deionized water, 0.005% t-Octylphenoxypolyethoxyethanol, and 0.005% t-Octylphenoxypolyethoxyethanol plus $10^{-5}$% Sodium Dodecyl Sulfate.

6. The method of claim 1, wherein said bioluminescent reagent comprises a luciferin/luciferase reagent.

7. The method of claim 1, wherein said microbial ATP extracting reagent comprises methanol mixed with 0.1 to 5% by weight of ammonium hydroxide.

8. The method of claim 1, wherein said microbial ATP extracting reagent comprises ethanol mixed with 0.1 to 5% by weight of ammonium hydroxide.

9. The method of claim 1, wherein one or more of said ATP hydrolyzing enzymes, for treating said extracted mammalian ATP, comprises adenosine triphosphatase (ATPase).

10. A method for rapidly detecting and enumerating microorganisms, having a level of microbial adenosine triphosphate (ATP), in mammalian cell cultures, comprising the steps of,
    providing a mammalian cell culture comprising mammalian cells having a level of mammalian ATP;
    reducing said level of mammalian ATP in said cell culture by,
        selectively lysing said mammalian cells and not lysing microbial cells by osmotically shocking said cells to extract said mammalian ATP, and
        treating said extracted mammalian ATP with one or more ATP hydrolyzing enzymes;
    immobilizing said microorganisms and washing away said hydrolyzing enzyme by filtering said mammalian cell culture through a micropartioned hydrophilic/hydrophobic membrane;
    extracting said microbial ATP using an extracting reagent;
    drying said membrane;
    applying a bioluminescent reagent onto said membrane; and
    detecting and enumerating said microorganisms.

11. The method of claim 10, after said step of lyzing said mammalian cells, further comprising the step of incubating said cell culture for about 15 minutes at room temperature.

12. The method of claim 10, after said step of filtering said cell culture, further comprising the step of incubating said membrane, through which said cell culture was filtered, for about 8–24 hours at about 25–35° C.

13. The method of claim 10, wherein said bioluminescent reagent comprises a luciferin-luciferase reagent.

14. The method of claim 10, wherein said microbial ATP extracting reagent comprises methanol mixed with 0.1 to 5% by weight of ammonium hydroxide.

15. The method of claim 10, wherein said microbial ATP extracting reagent comprises ethanol mixed with 0.1 to 5% by weight of ammonium hydroxide.

16. The method of claim 10, wherein said membrane is dried at temperatures between ambient temperature and 40° C.

17. The method of claim 10, wherein one or more of said ATP hydrolyzing enzymes, for treating said extracted mammalian ATP, comprises adenosine triphosphatase (ATPase).

18. A method for rapidly detecting and enumerating microorganisms, having a level of microbial adenosine triphosphate (ATP), in mammalian cell cultures, comprising the steps of, provident a mammalian cell culture comprising mammalian cells having a level of mammalian ATP;

reducing said level of mammalian ATP in said cell culture by, selectively lysing said mammalian cells and not lysing microbial cells with one or more detergents to extract said mammalian ATP, treating said extracted mammalian ATP with one or more ATP hydrolyzing enzymes, and incubating said cell culture for about 15 minutes at room temperature;

immobilizing said microorganisms and washing away said detergent and said hydrolyzing enzyme by filtering said mammalian cell culture through a micropartioned hydrophilic/hydrophobic membrane;

incubating said membrane, through which said cell culture was filtered, for about 8–24 hours at about 25–35° C.;

extracting said microbial ATP using an extracting reagent;

drying said membrane;

applying a luciferin-luciferase reagent onto said membrane; and detecting and enumerating said microorganisms.

19. The method of claim 18, wherein said detergents comprise one or more detergents selected from the group consisting of 2% Polyoxyethylenesorbitan Monooleate, 13% Polyoxyethylenesorbitan Monooleate, deionized water, 0.005% t-Octylphenoxypolyethoxyethanol, and 0.005% t-Octylphenoxypolyethoxyethanol plus $10^{-5}$% Sodium Dodecyl Sulfate.

20. The method of claim 18, wherein said microbial ATP extracting reagent comprises methanol mixed with 0.1 to 5% by weight of ammonium hydroxide.

21. The method of claim 18, wherein said microbial ATP extracting reagent comprises ethanol mixed with 0.1 to 5% by weight of ammonium hydroxide.

22. The method of claim 18, wherein said membrane is dried at temperatures between ambient temperature and 40° C.

23. The method of claim 18, wherein one or more of said ATP hydrolyzing enzymes, for treating said extracted mammalian ATP, comprises adenosine triphosphatase (ATPase).

24. A method for reducing the level of background ATP in a mammalian cell culture for subsequent detection of microorganisms, having a level of microbial adenosine triphosphate (ATP), comprising the steps of, providing a mammalian cell culture comprising mammalian cells having a level of mammalian ATP;

reducing said level of mammalian ATP in said cell culture by, selectively lysing said mammalian cells and not lysing microbial cells with one or more detergents to extract said mammalian ATP, and treating said extracted mammalian ATP with one or more AT? hydrolyzing enzymes; and immobilizing said microorganisms and washing away said detergent and said hydrolyzing enzyme by filtering said mammalian cell culture through a hydrophilic/hydrophobic membrane.

25. The method of claim 24, wherein said detergents comprise one or more detergents selected from the group consisting of 2% Polyoxyethylenesorbitan Monooleate, 13% Polyoxyethylenesorbitan Monooleate, deionized water, 0.005% t-Octylphenoxypolyethoxyethanol, and 0.005% t-Octylphenoxypolyethoxyethanol plus $10^{-5}$% Sodium Dodecyl Sulfate.

26. The method of claim 24, wherein one or more of said ATP hydrolyzing enzymes, for treating said extracted mammalian ATP, comprises adenosine triphosphatase (ATPase).

* * * * *